US009138576B2

(12) United States Patent
Klardie et al.

(10) Patent No.: US 9,138,576 B2
(45) Date of Patent: Sep. 22, 2015

(54) LEAD END HAVING INNER SUPPORT

(71) Applicant: Medtronic, Inc., Minneapolis, MN (US)

(72) Inventors: Michael R. Klardie, Plymouth, MN (US); Daniel C. Oster, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 123 days.

(21) Appl. No.: 13/663,080

(22) Filed: Oct. 29, 2012

(65) Prior Publication Data

US 2013/0109254 A1 May 2, 2013

Related U.S. Application Data

(60) Provisional application No. 61/552,911, filed on Oct. 28, 2011.

(51) Int. Cl.
| | |
|---|---|
| *A61N 1/00* | (2006.01) |
| *A61B 5/04* | (2006.01) |
| *A61N 1/05* | (2006.01) |
| *H01R 24/58* | (2011.01) |
| *H01R 43/24* | (2006.01) |
| *A61N 1/36* | (2006.01) |
| *H01R 107/00* | (2006.01) |

(52) U.S. Cl.
CPC ............ *A61N 1/0534* (2013.01); *A61N 1/0551* (2013.01); *A61N 1/3605* (2013.01); *H01R 24/58* (2013.01); *H01R 43/24* (2013.01); *H01R 2107/00* (2013.01); *H01R 2201/12* (2013.01)

(58) Field of Classification Search
USPC .................................... 607/119, 122; 600/372
See application file for complete search history.

(56) References Cited

U.S. PATENT DOCUMENTS

| | | | |
|---|---|---|---|
| 5,458,629 | A | 10/1995 | Baudino et al. |
| 5,935,159 | A | 8/1999 | Cross, Jr. et al. |
| 7,108,549 | B2 | 9/2006 | Lyu et al. |
| 7,184,838 | B2 | 2/2007 | Cross, Jr. |
| 7,184,840 | B2 | 2/2007 | Stolz et al. |
| 7,326,083 | B2 | 2/2008 | Mehdizadeh et al. |

(Continued)

FOREIGN PATENT DOCUMENTS

| | | |
|---|---|---|
| WO | WO2013/062863 | 5/2006 |
| WO | WO2008/060142 | 5/2008 |
| WO | WO2013/062859 | 5/2013 |

OTHER PUBLICATIONS

PCT/US12/060935: Search Report and Written Opinion dated Jan. 23, 2013.

(Continued)

*Primary Examiner* — Nicole F Lavert
(74) *Attorney, Agent, or Firm* — Withers & Keys, LLC

(57) ABSTRACT

Various embodiments of this disclosure concern a lead end having an inner support. Such a lead can include a first end, a second end, a main body, and a plurality of exposed electrical elements on each of the lead ends. A metal support can be contained within the first end, the metal support comprising a plurality of longitudinal members and a plurality of cross members between the longitudinal members, the metal support having an interior space. The first lead end can further include polymer fill within the interior space of the metal support and encapsulating at least a substantial portion of the metal support, the polymer fill defining at least some of the exterior surface of the first end between the exposed electrical elements of the first end.

15 Claims, 12 Drawing Sheets

(56) References Cited

U.S. PATENT DOCUMENTS

| | | |
|---|---|---|
| 7,437,197 B2 | 10/2008 | Harris et al. |
| 7,499,755 B2 | 3/2009 | Cross, Jr. et al. |
| 7,680,544 B1 | 3/2010 | Conger |
| 7,797,057 B2 | 9/2010 | Harris |
| 2004/0097965 A1 | 5/2004 | Gardeski et al. |
| 2005/0182470 A1 | 8/2005 | Cross, Jr. |
| 2005/0234522 A1 | 10/2005 | Ley et al. |
| 2007/0168004 A1 | 7/2007 | Walter |
| 2008/0147158 A1* | 6/2008 | Zweber et al. ............ 607/122 |
| 2009/0012591 A1 | 1/2009 | Barker |
| 2009/0143846 A1 | 6/2009 | Cross, Jr. |
| 2009/0222073 A1 | 9/2009 | Flowers et al. |
| 2009/0234407 A1 | 9/2009 | Hastings et al. |
| 2010/0305670 A1 | 12/2010 | Hall et al. |
| 2011/0022100 A1 | 1/2011 | Brase et al. |
| 2011/0072659 A1 | 3/2011 | Swanson et al. |
| 2011/0106189 A1 | 5/2011 | Seeley et al. |
| 2011/0165785 A1 | 7/2011 | Lindner et al. |
| 2011/0220408 A1 | 9/2011 | Walsh et al. |

OTHER PUBLICATIONS

PCT/US12/060988: Search Report and Written Opinion dated Jan. 31, 2013.

* cited by examiner

LEAD END HAVING INNER SUPPORT

TECHNICAL FIELD

The disclosure relates to medical leads, including implantable leads configured to conduct electrical energy between tissue and circuitry.

BACKGROUND OF THE INVENTION

Leads can be used to carry electrical energy between tissue and circuitry of a device, such as in sensing and/or stimulation applications. In the case of sensing, the electrical energy may be indicative of physiological activity while in a case of therapy delivery the electrical energy may comprise stimulation pulses. Leads may be partially or wholly implanted within a patient. For example, an implanted lead can carry electrical signals generated in a patient (e.g., brain, heart, muscles) to signal processing circuitry in an implanted housing for data collection and/or determination of a patient state. Additionally or alternatively, electrical stimulation can be delivered from stimulation circuitry within the housing to a targeted area of the patient (e.g., brain, heart, spine, one or more nerves, pelvic floor, muscles) through the lead. Typically, the lead and the housing are separate components that are connected to one another during an implantation procedure.

SUMMARY

In general, this disclosure concerns medical leads having a support for one or both ends of the leads.

Various embodiments concern leads comprising a first end, a second end, and a main body connecting the first end and the second end, the first end having a first plurality of exposed electrical elements and the second end having a second plurality of exposed electrical elements, at least some of the exposed electrical elements on the first end respectively electrically connected to at least some of the exposed electrical elements of the second end by a plurality of electrical conductors in the main body. Such leads can further comprise a metal support within the first end, the metal support comprising a plurality of longitudinal members generally parallel with the axis of first end of the lead and a plurality of cross members between the longitudinal members, wherein the metal support has an interior space, extends proximal and distal of the plurality of exposed electrical elements of the first end, and is electrically isolated from the exposed electrical elements of the first end. Such leads can further comprise polymer fill within the interior space of the metal support and encapsulating at least a substantial portion of the metal support, the polymer fill defining at least some of the exterior surface of the first end between the exposed electrical elements of the first end.

In some lead embodiments, the metal support is a unitary body. In some lead embodiments, the cross members form a plurality of rings that are aligned axially with the axis of the first end of the lead.

The metal support may comprise a plurality of grip features, each of the grip features comprising at least one of the cross members that is surrounded by the polymer fill to provide mechanical fixation between the polymer fill and the metal support. In some cases, at least one grip feature is located proximal along the lead with respect to the most proximal exposed electrical element of the first end and another grip feature is located distal along the lead with respect to the most distal exposed electrical element of the first end.

In some lead embodiments, the metal support comprises a plurality of windows defined by the longitudinal members and the cross members. In some cases, the conductors run through the windows, the conductors bridging the electrical connections between the exposed electrical elements of the first and second ends. In some cases each of the windows is filled in with the polymer fill.

In some lead embodiments, each exposed electrical element of the first end comprises a contact ring that surrounds the metal support and defines at least some of the exterior surface of the first end. In some cases, each contact ring comprises a proximal end and a distal end, and the polymer fill directly contacts each of the proximal and distal ends of each contact ring to prevent the rings from moving proximally or distally along the lead.

In some lead embodiments, the first end is configured to plug into an implantable medical device and the exposed electrical elements of the first end are arrayed to electrically connect with respective channels of the implantable medical device.

The lead may comprise a metal zero contact having a window and a flange, the metal zero contact at least partially overlapping with the support member, the metal zero contact being mechanically fixed to the metal support by the polymer fill filling the window of the metal zero contact.

The metal support provides a majority of the axial strength of the first end in some cases. A lumen within the first end and the main body may be present in some cases, the lumen extending within the metal support and open on the first end of the lead. In some cases, the plurality of cross members comprise sections of a spring welded to the plurality of longitudinal members.

Some embodiments concern methods for making a lead comprising loading a plurality of electrical elements onto a metal support, the metal support comprising a plurality of longitudinal members and a plurality of cross members between the longitudinal members, the metal support having an interior space and being electrically insulated by a coating. Such methods may further comprise connecting a plurality of conductors to the plurality of electrical elements, and injecting polymer fill into the interior space of the metal support to encapsulate at least a substantial portion of the metal support, the polymer fill being deposited in between the plurality of electrical elements to define an exterior surface of a lead body, the plurality of conductors within the interior space when the polymer fill is injected. Methods may include removing sections from a metal hypo tube to make the metal support.

In some cases, loading the plurality of electrical elements onto the metal support comprises aligning the contact rings with respective cross members of the metal support. Methods may further comprise tacking the electrical elements in alignment with the respective cross members with medical adhesive.

Some of the methods further include placing a core pin within the interior space of the metal support before injecting the polymer fill, the core pin extending proximally from the proximal end of the metal support and distally from the distal end of the metal support, and removing the core pin following injection of the polymer fill to leave a lumen within the lead body.

In some embodiments, loading the plurality of electrical elements onto the metal support comprises placing a plurality of contact rings over the metal support such that the contact rings are arrayed along the metal support.

In some embodiments, connecting the plurality of conductors to the plurality of electrical elements comprises welding the conductors to the electrical elements. In some cases, the plurality of electrical elements are loaded onto the metal support such that at least one grip feature of the metal support is proximal with respect to the most proximal electrical element and another grip feature of the metal support is distal with respect to the most distal electrical element, wherein each grip feature comprises at least one of the cross members that becomes encapsulated by the injected polymer fill.

In various embodiments, the metal support includes a plurality of windows defined by the longitudinal members and the cross members, and each of the window is filled in by the injected polymer fill.

In some cases, each electrical element comprises a proximal end and a distal end, and the polymer fill is injected to directly contact each of the proximal and distal ends of each electrical element to prevent the electrical elements from moving proximally or distally along the lead upon solidification of the polymer fill.

Some embodiments include placing a metal zero contact at least partially over the metal structure, the metal zero contact having a window and a flange, and injecting polymer material to fill in the window of the metal zero contact and surround at least one cross member of the metal structure to mechanically fix the metal structure to the metal zero contact.

The details of one or ore examples are set forth in the accompanying drawings and the description below. Other features, objects, and advantages will be apparent from the description and drawings, and from the claims.

DETAILED DESCRIPTION OF THE INVENTION

Figure 1:
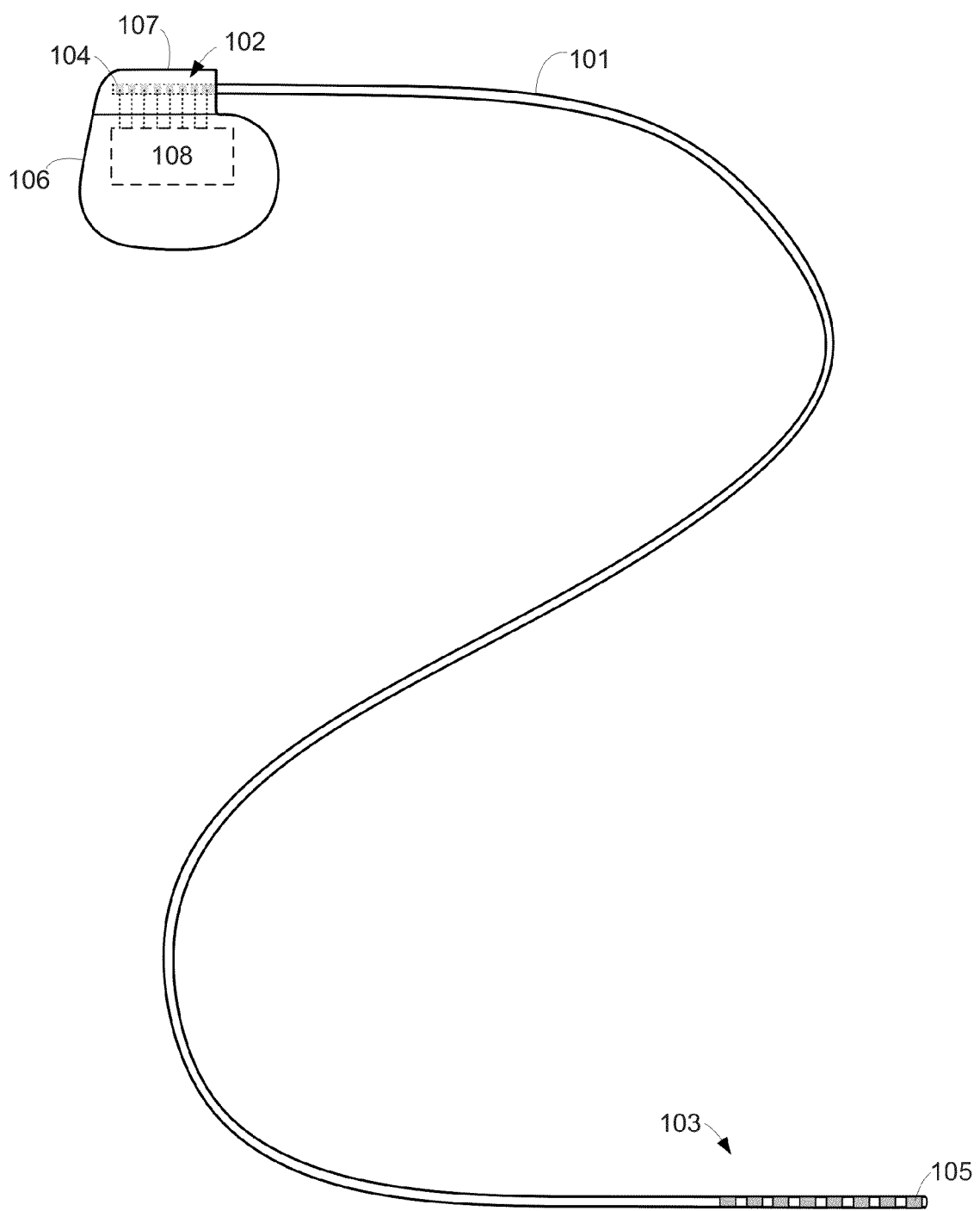
FIG. 1 illustrates a lead and implantable device for one or both of sensing signals and delivering stimulation.

FIG. 1 illustrates a lead 101 plugged into an implantable medical device (IMD) 106. The lead 101 includes a proximal end 102 and a distal end 103. A number of electrodes are on the distal end 103 of the lead 101 (such as ring electrode 105) while a number of contacts are on the proximal end 102 of the lead 101 (such as contact ring 104). A plurality of conductors, which are not shown in FIG. 1 because they are fully contained within the body of the lead 101, electrically connect respective contacts of the proximal end 102 with electrodes of the distal end 103.

The IMD 106 can be configured for stimulating tissue (e.g., as a brain stimulator, spinal stimulator, peripheral nerve stimulator, pelvic nerve stimulator, cardiac stimulator, muscle stimulator, or any other type of stimulator configured to deliver electrical energy). The IMD 106 may additionally or alternatively be configured to sense one or more bioelectrical signals received by one or more electrodes and conducted through the lead 101 (e.g., nerve signals, local field potential signals, cardiac signals, electromyogram signals, or any other physiologic signals).

When the proximal end 102 of the lead 101 is plugged into the header 107 of the IMD 106, electrical connections are made between conductors of the lead 101 and circuitry 108 of the IMD 106. Circuitry 108 may include signal processing circuitry, stimulation circuitry, a controller, memory, and/or a switch matrix. The electrical connections between the IMD 106 and the lead 101 are made by metal conductors within the header 107 of the IMD 106 touching respective contacts (e.g., contact 104) of the proximal end 102 of the lead 101. At least part of the proximal end 102 of the lead 101 is inserted into the header 107 to make the physical connections between the contacts of the lead 101 and the electrical conductors of the IMD 106. The exposed contacts of the proximal end 102 of the lead 101 are arrayed to physically connect with different metal conductors within the header 107, each of the different metal conductors of the header 107 electrically connecting with different stimulation and/or sensing channels of the IMD 106.

The header 107 includes an opening to allow insertion of the proximal end 102 of the lead 101 into the header 107. In various embodiments, the opening is only slightly larger in diameter then the proximal end 102 of the lead to minimize the amount of space for bodily fluids to enter the header 107. Furthermore, seals can be located within the header 107, around the proximal end 102 of the lead 101, to limit bodily fluids from shorting electrical circuits. Electrical signals are conducted between the header 107 and circuitry 108 by a feedthrough that bridges between the housing of the IMD 106 and the header 107.

The main body of the lead 101, which is between the proximal end 102 and the distal end 103 of the lead 101, is relatively flexible to allow the lead 101 to be implanted along curved paths within the body. Furthermore, flexibility of the main body allows the lead 101 to accommodate the movements of the body (e.g., along the neck or the back of a patient).

While it can be advantageous to have a relatively flexible main body of the lead 101, it can also be advantageous to have the proximal end 102 of the lead 101 be relatively stiff. Some resistance in inserting the proximal end 102 of the lead 101 into the header 107 can be experienced because of the close fit between the outer diameter of the proximal end 102 and the inner diameter of the space within the header 107. Moreover, resistance may be experienced as the proximal end 102 may have to overcome seals or other leakage barriers upon inserting the proximal end 102 into the header 107. Such resistance could risk kinking of the proximal end 102, slipping of the physician's grip on the proximal end 102, and/or uncertainly over whether the proximal end 102 is fully inserted within the header 107.

The present disclosure concerns, among other things, leads having an end that is reinforced by a support within the lead end. For example, the proximal end 102 and/or the distal end 103 of the lead 101 may contain such a support. The support can, among other things, stiffen the end of the lead. For example, a stiff proximal end 102 can more easily overcome obstacles (e.g., seals) resisting insertion, thereby facilitating easier insertion of the proximal end 102 into the header 107. A stiff proximal end 102 can also serve has a firm and robust handle for a physician in inserting the proximal end 102 into the header 107. Also, a stiff proximal end 102 can maintain its integrity during insertion, where a more flexible end may be too floppy or prone to kinking to quickly and confidently insert into the header 107 during an implantation procedure.

Figure 2:
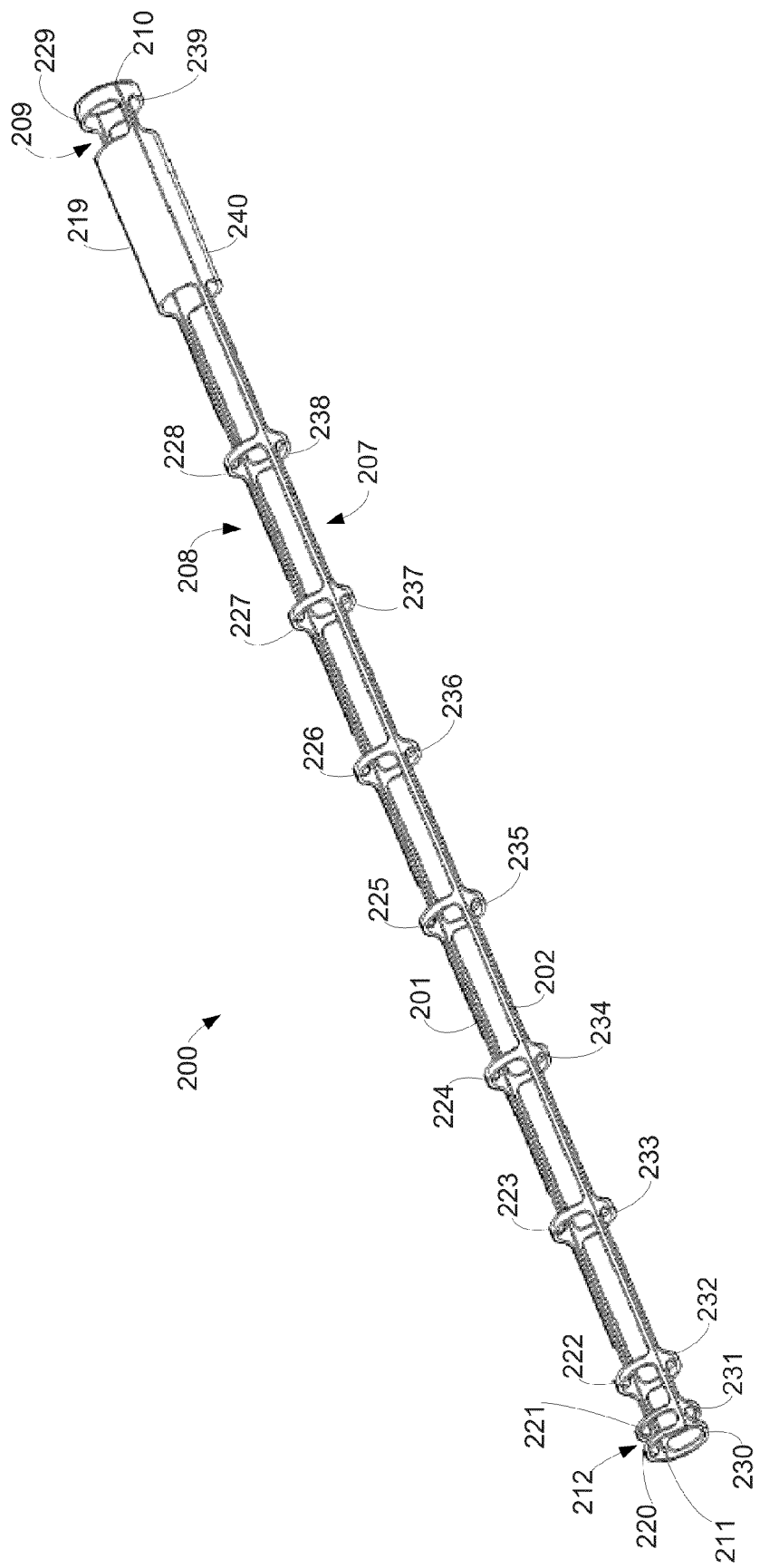
FIG. 2 illustrates an embodiment of a support.

FIGS. 2-12 show a process for forming a proximal end of a lead, such as the proximal end 102 of the lead 101 of FIG. 1. It is noted that the techniques demonstrated in FIGS. 2-12 may be used to construct a distal end 103 of a lead 101. FIG. 2 illustrates a support 200. In various embodiments, the support 200 is made entirely of metal, and in some cases the metal is coated by a polymer to electrically insulate the metal support 200. For example, the support 200 may be entirely coated by parylene or other poly(p-xylylene) polymer deposited by a chemical vapor. A polymer coating, such as urethane or other polymer, may be coated over the support 200 by a spray or dip coating process. In some cases, the support 200 is made from polymer and/or other material.

The support 200 of FIG. 2 includes two longitudinal members 201 and 202. Although the support 200 illustrated in FIG. 2 has two longitudinal members 201 and 202, a different number of longitudinal members are contemplated for various other embodiments, such as one, three, four, five, six, ten, or another number of longitudinal members. As shown in FIG. 2, each longitudinal member 201 and 202 fully extends from the proximal end 211 of the support 200 to the distal end 210 of the support 200. In some embodiments each longitudinal members extends the full length of the support, while in some other embodiments one, some, or all of the longitudinal supports do not extend the full length of the support 200.

The support 200 further includes a plurality of cross members 219-229 and 230-240. In various embodiments of the present disclosure, the cross members are transverse to the longitudinal members, and in some embodiments the cross members are perpendicular to the longitudinal members where the cross members join the longitudinal members at right angles. In some embodiments, cross members 219-229 and 230-240 span laterally from one side of the support 200 to the other side of the support 200. In some embodiments, the cross members 219-229 and 230-240 span laterally from one side of the support 200 to the other side of the support 200 in an arc, as shown in FIG. 2. The arrangement of arcing cross members 219-229 and 230-240 arrayed along the longitudinal members 201 and 202 forms a generally tubular support 200, with the arcing cross members 219-229 and 230-240 and the longitudinal members 201 and 202 forming a skeletal structure of the generally tubular support 200. An interior space is provided within the tubular support 200.

As shown in FIG. 2, the cross members 219-229 and 230-240 join the longitudinal members 201 and 202 into a single body. As further shown in FIG. 2, each of the cross members 219-229 and 230-240 has an arc shape. For example, top cross members 219-229 form arcs above the longitudinal members 201 and 202 while bottom cross members 230-240 form arcs below the longitudinal members 201 and 202. As such, an interior space exists within the support 200. In the case of the embodiment of FIG. 2, the interior space is bounded laterally by longitudinal supports 201 and 202 and vertically by arcing cross members 219-229 and 230-240. As such, an interior space of various supports can be defined as the space within longitudinal members and cross members.

Longitudinal members and cross members of a support can also define windows. For example, window 208 is defined by the longitudinal members 201 and 202 and top cross members 227 and 228. The window 208 provides access to the interior space of the support 200 from the top of the support 200. Window 207 is defined by the longitudinal members 201 and 202 and bottom cross members 237 and 238. The window 207 provides access to the interior space of the support 200 from the bottom of the support 200. Many other windows provide access to the interior space of the support 200, including windows 212 and 209.

Supports as described herein can be made in various ways. A metal support, such as support 200 of FIG. 2, can be made by first forming a hypo tube (e.g., out of stainless steel). Windows (e.g., windows 208, 209, and 212) can be formed in the hypo tube by removing the window sections of the hypo tube, thereby leaving cross members and longitudinal members. For example, the windows can be mechanically machined, electrically machined (e.g., by electrical discharge machining), laser cut, or removed by another technique. A polymer support can be injection molded or cut from an extruded tube, the cutting of the windows being done using one or more of the techniques used to cut windows of a metal support as described above. As discussed further herein, a metal support can be coated by an insulating polymer. A metal support could be uncoated if it is made of a material with a very high impendence, such as tungsten. Suitable metals for making a support include, but are not limited to, stainless steel, titanium, and nickel-titanium alloy.

Figure 3:
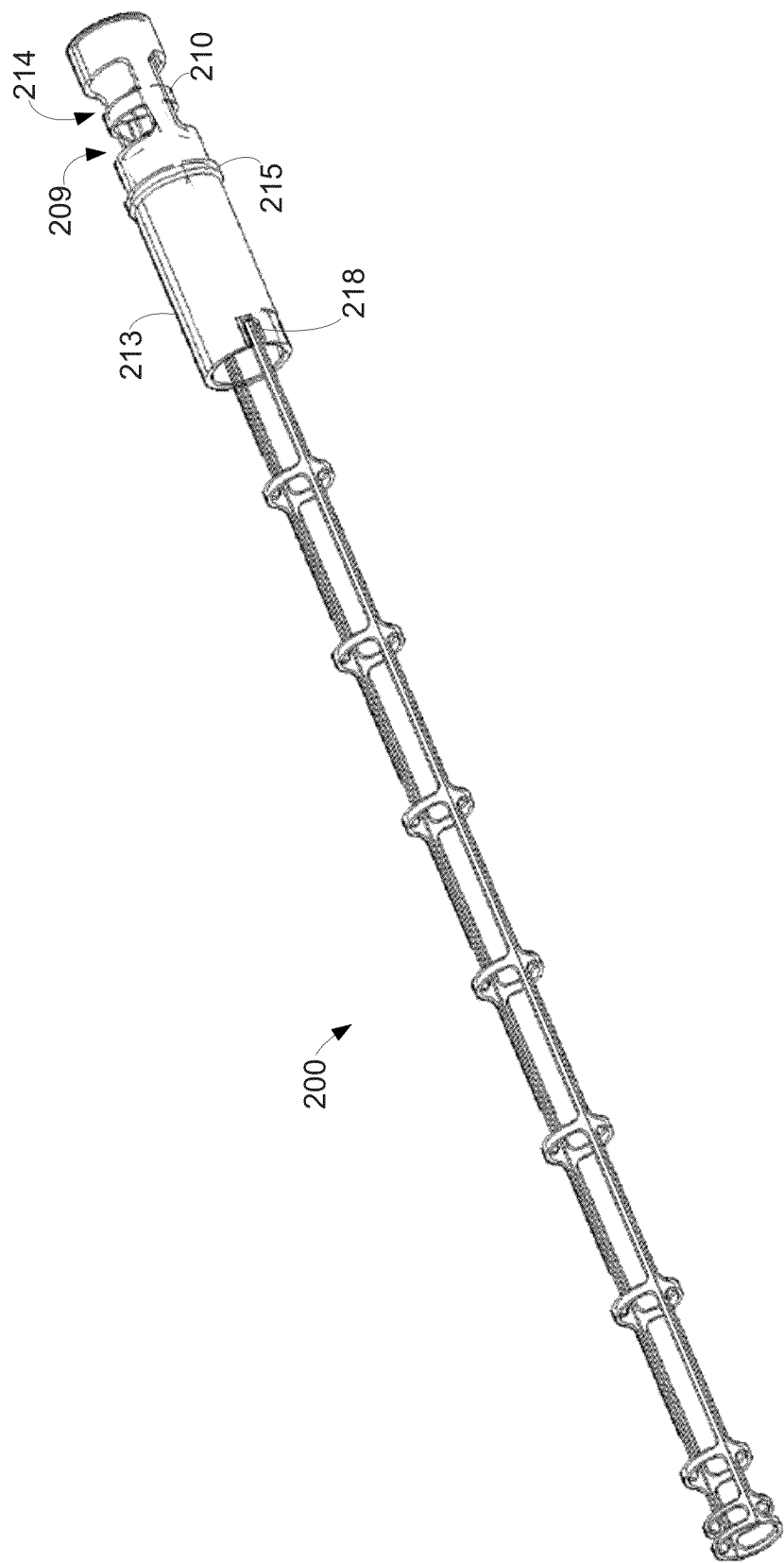
FIG. 3 illustrates a support and a zero contact.

FIG. 3 illustrates a zero contact 213 placed over the distal end 210 of the support 200. The zero contact 213 can be associated with several functions. In some embodiments the zero contact 213 can be spaced along a proximal lead end and configured to make an electrical connection with an electrical element in a header. The zero contact 213 can further be connected to a conductor in a lead and electrically connected with an electrode on the distal end of a lead for stimulation and/or sensing. A slot 218 is provided in the zero contact 213 for connecting the zero contact 213 to the conductor which electrically connects with a distal end electrode. The use of the slot 218 for making an electrical connection is further discussed herein. The zero contact 213 can additionally or alternatively seal an opening of a header when the proximal end of a lead is inserted into the header. For example, flange 215 may engage with part of an opening of a header to inhibit fluids from entering the opening and penetrating the header. The flange 215 may additionally or alternatively prevent a proximal end of a lead from being inserted too far into a header.

The zero contact 213 may also facilitate connecting parts of a lead together. For example, zero contact 213 includes window 214, which is partially aligned with the window 209 of the support 200. The window 214 of the zero contact 213 provides access to the interior space of the zero contact 213. A core pin (not illustrated) can further be inserted into the interior spaces of both the support 200 and the zero contact 213. The subassembly of the support 200, zero contact 213, and core pin can be placed in a die of an injection mold. Polymer fill material can then be injected into the interior spaces of the support 200 and the zero contact 213 (e.g., flowing through the window 214 of the zero contact 213 and then through the window 209 of the support 200).

Figure 4:
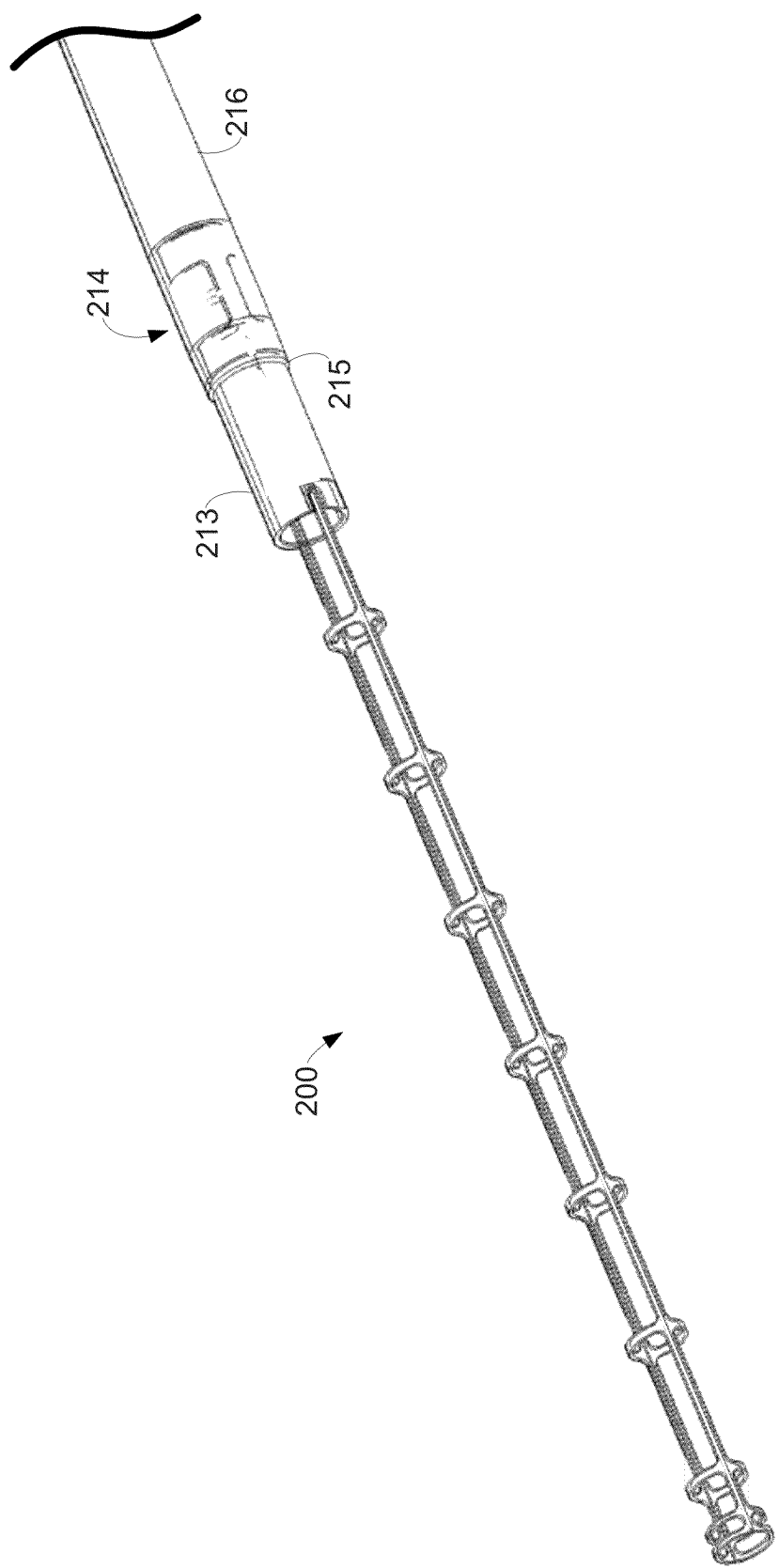
FIG. 4 illustrates a support and zero contact subassembly.

FIG. 4 illustrates the support 200 and zero contact 213 after the injection of polymer fill. As shown in FIG. 4, the window 214 of the zero contact 213 has been filled in with polymer fill and the polymer fill has further defined a cylindrical exterior section 216. As such, the polymer fill material can also define an exterior section 216 of a lead overlapping and distal to the zero contact 213, the exterior section 216 being defined by the interior of the injection molding die. The exterior section 216 can have several functions. For example, the exterior section can serve as a handle for a physician to grip while inserting the proximal end of the lead into a header. The exterior section can additionally or alternatively be used for attaching a tube of the main body of the lead. The tube, such as a tantalum braided polymer tube, can span most of the length of the lead connecting the proximal end of the lead with the distal end. The tube can allow conductors to run between the proximal and distal ends to conduct electrical energy between contacts of the proximal end and electrodes of the distal end. The tube can be bonded to the exterior section 216 by a butt bond using a shrink tube and applied heat, a lap joint, a laser bond, or a combination of these bonding techniques.

In some embodiments, the exterior section 216, the zero contact 213, the flange 215, and/of the support 200 can be longitudinally spaced to align with a feature of an IMD during insertion of a lead proximal end into a head. The feature of the IMD may be the end of the IMD or an opening of a header. Such alignment can serve as in indicator to a physician showing when the proximal lead has been fully inserted into a header opening. Such an indicator can provide assurance that a proximal end has been fully inserted while minimizing further pushing by the physician once the proximal end is fully inserted. The exterior section 216, the zero contact 213, the flange 215, and/or the support 200 can be colored differently than the rest of the lead to distinguish it as an insertion indicator. In some embodiments, the support 200 can be seen through a window (e.g., window 214) or felt as a stiff section within the lead by a physician when serving as an insertion indicator.

The distal end of the zero contact 213 has a smaller diameter than the injection molding die. Therefore, the polymer fill material fills in the gap between the zero contact 213 and the injection molding die. As such, the entire portion of the zero contact 213 distal of the flange 215 has been surrounded and encapsulated by polymer fill. The polymer fill can be a transparent polymer such that the distal end of the zero contact 213 is still visible under a layer of polymer fill as shown in FIG. 4.

The window 214 of the zero contact 213 provides a feature for the polymer fill to mechanically grip as the polymer fill hardens with cooling. Polymer fill can mechanically grip cross members and windows because the polymer fill can completely fill in the window and encapsulate other parts (e.g., the entire portion of the zero contact 213 distal of the flange 215). Moreover, the polymer fill can flow through the window 209 of the support 200, thereby forming a mechanical coupling of polymer fill between the support 200 and the zero contact 213, mechanically fixing the support 200 and the zero contact 213 to each other.

A lumen is defined within the subassembly of the support 200 and the zero contact 213 by the polymer fill after removal of the core pin, the inner diameter of the lumen dependent on the outer diameter of the core pin. The lumen can be used to accommodate various things within the subassembly of the support 200 and the zero contact 213, such as electrical conductors, as shown in FIG. 5.

Figure 5:
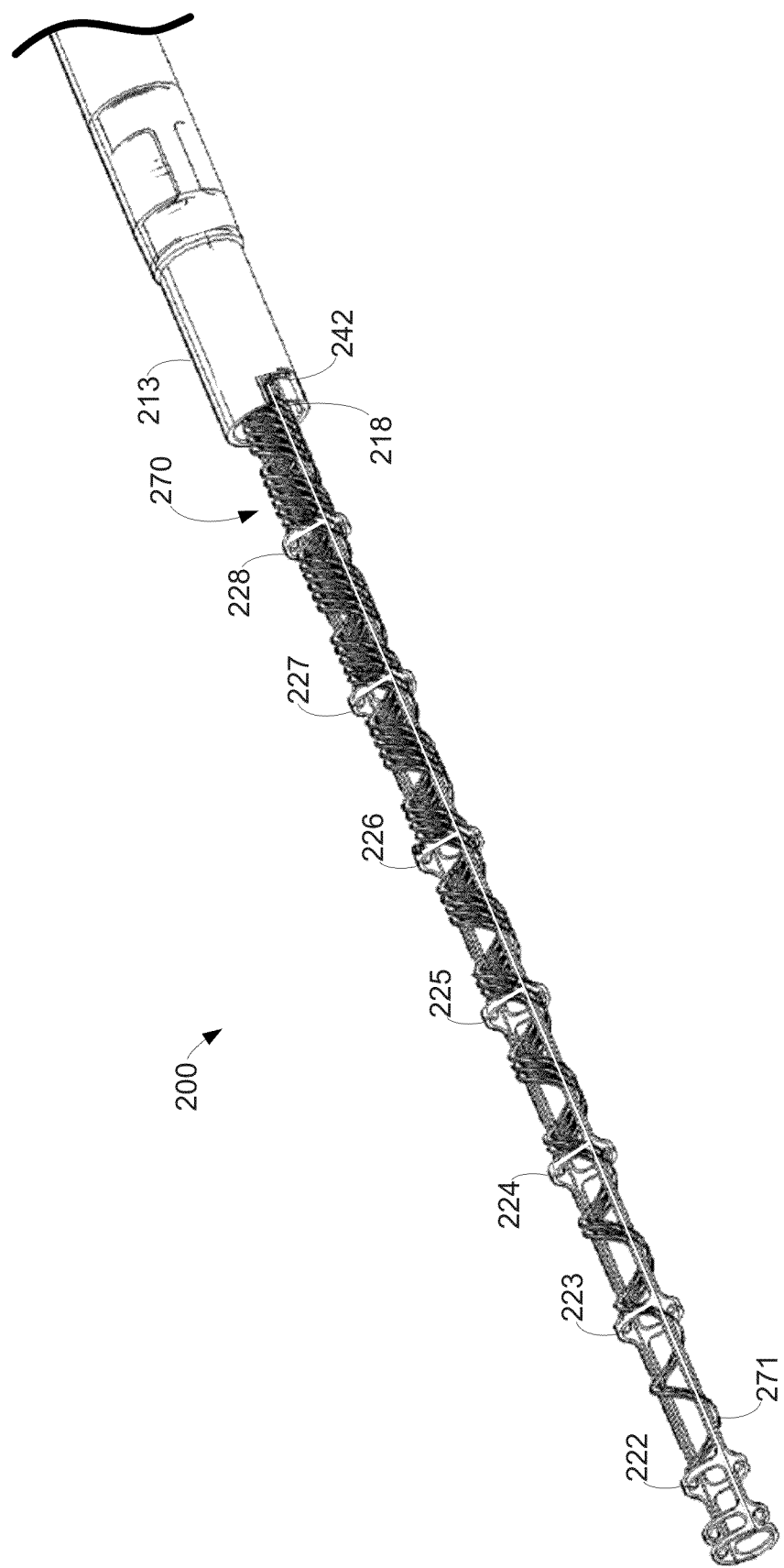
FIG. 5 illustrates a lead end subassembly.

FIG. 5 illustrates a set of conductors 270 run through the lumen of the subassembly of the support 200 and the zero contact 213. Each conductor of the set of conductors 270 can be an individual metal filar, for example. Each conductor can be made of metal or other conductive material and can be configured to conduct electrical energy (e.g., stimulation pulses and/or bioelectrical signals) along a lead. Each conductor can further be coated to insulate the metal filar to prevent electrical shorting. The set of conductors 270 can be wound around a mandrel over a length to create the helical pattern of conductors shown in FIG. 5 before being routed through the subassembly of the support. 200 and the zero contact 213. The helical pattern of the conductors 270 can be convenient for routing the set of conductors 270 through the lumen of the subassembly because the helical pattern can maintain a core space in the lumen. The core space can be maintained because, in some embodiments, the coiled conductors 270 will tend to brace against the inner surface of the lumen.

Each of the conductors can be cut to a different length. The different lengths can correspond to which electrical elements the conductors will be respectively connected. The length to which the conductors are cut can be based on the cross members 222-228. For example, conductor 271 can be cut to terminate at or near cross member 222. Specifically, conductor 271 may be cut at or near that point at which it lines up with cross member 222. As each conductor of the set of the conductors 270 is cut to a different length corresponding to a different cross member 222-228, the conductors get fewer in number proximally. For example, conductor 271 is the last conductor proximally.

Conductor 242 is cut to align with the slot 218 of the zero contact 213. The conductor 242 can then be bent back and placed within the slot 218 of the zero contact 213. The slot 218 provides some containment of the proximal end of the conductor 242, wherein the conductor 242 may otherwise tend to spring back into the set of conductors 270. The conductors 270 will tend to retain the coil shape shown in FIG. 5, and each conductor pulled from this group any may resist being pulled from helical alignment with the other conductors 270. As such, placing an individual conductor in a slot may help anchor and keep the conductor in place before the conductor is permanently attached to an electrical element.

Conductor 242 can be welded to the zero contact 213 while the proximal end of the conductor 242 is within the slot 218 of the zero contact 213. The welding process can create a small pool of molten metal around the proximal end of the conductor 242 and the slot 218 to permanently and electrically connect the conductor 242 to the zero contact 213. This welding technique can be repeated for other electrical elements, including contact rings, placed on the subassembly of the support 200 and the zero contact 213.

Figure 6:
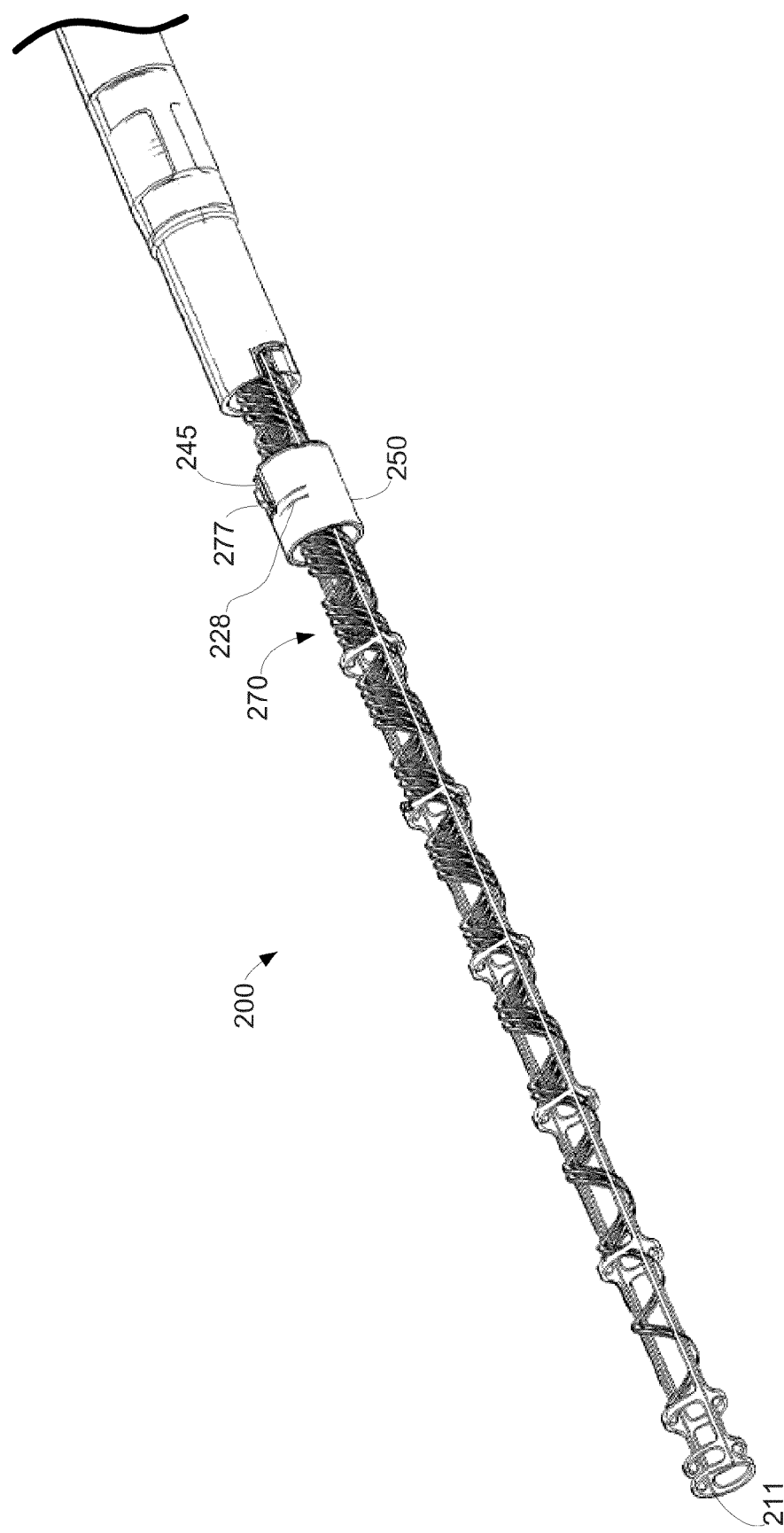
FIG. 6 illustrates an electrical element on a lead end subassembly.

FIG. 6 shows that a contact ring 250 has been slide over the proximal end 211 of the support 200 and aligned with cross member 228 (the cross member 228 is shown through the contact ring 250 in FIG. 6). The proximal end of the conductor 277, cut to length at or near the cross member 228, is placed in the slot 245 of the contact ring 250. Once the proximal end of the conductor 277 is within the slot 245, the conductor 277 can be welded to permanently and electrically connect the conductor 277 to the contact ring 250. As described herein, the welding process can create a small pool of molten metal around the proximal end of the conductor 277 and the slot 243, the pool cooling to solid metal.

Contact ring 250 can be aligned with cross member 228 in various ways. For example, the proximal end of the contact ring can be aligned with the proximal end of the cross member 228. Alternatively, the proximal end of the contact ring 250 can be aligned with the distal end of the cross member 228, the distal end of the contact ring 250 can be aligned with the distal end of the cross member 228, or the distal end of the contact ring 250 can be aligned with the proximal end of the cross member 228. In some cases, the middle of the contact ring 250 can be aligned with the middle of the cross member 228. In some embodiments, the proximal end of the slot 245 can be aligned with the cross member 228. As shown in FIG. 6, the contact ring 250 can be aligned with the cross member 228 such that the cross member 228 is fully overlapped by the contact ring 250.

Figure 7:
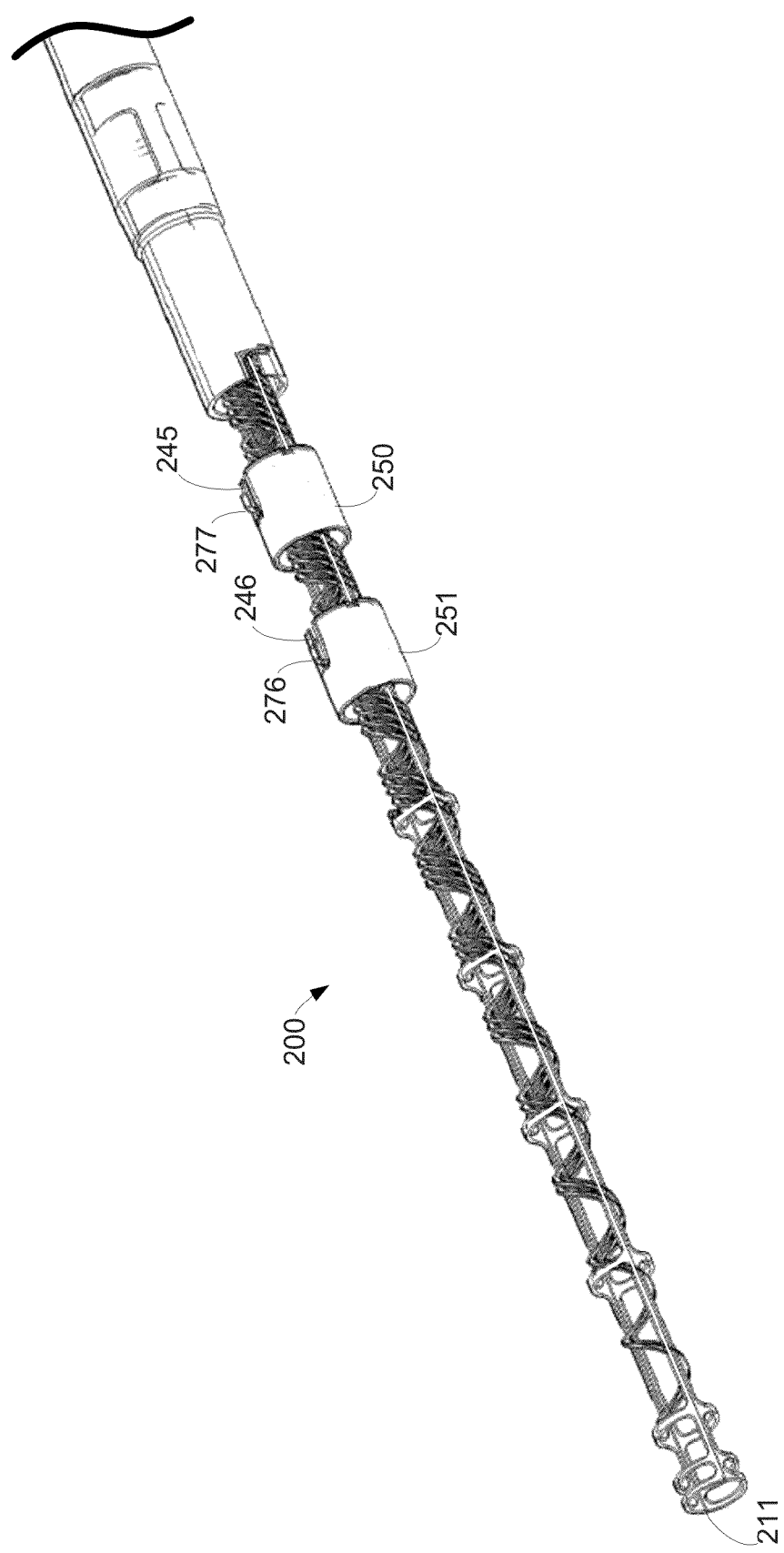
FIG. 7 illustrates multiple electrical elements on a lead end subassembly.

Other electrical elements, such as other contact rings, can be aligned with cross members in the same ways as contact ring 250 is aligned with cross member 228. FIG. 7 shows that another contact ring 251 has been slid over the proximal end 211 of the support 200 and into alignment with cross member 227 (shown in FIG. 2 but obscured by the contract ring 251 in FIG. 7).

Figure 8:
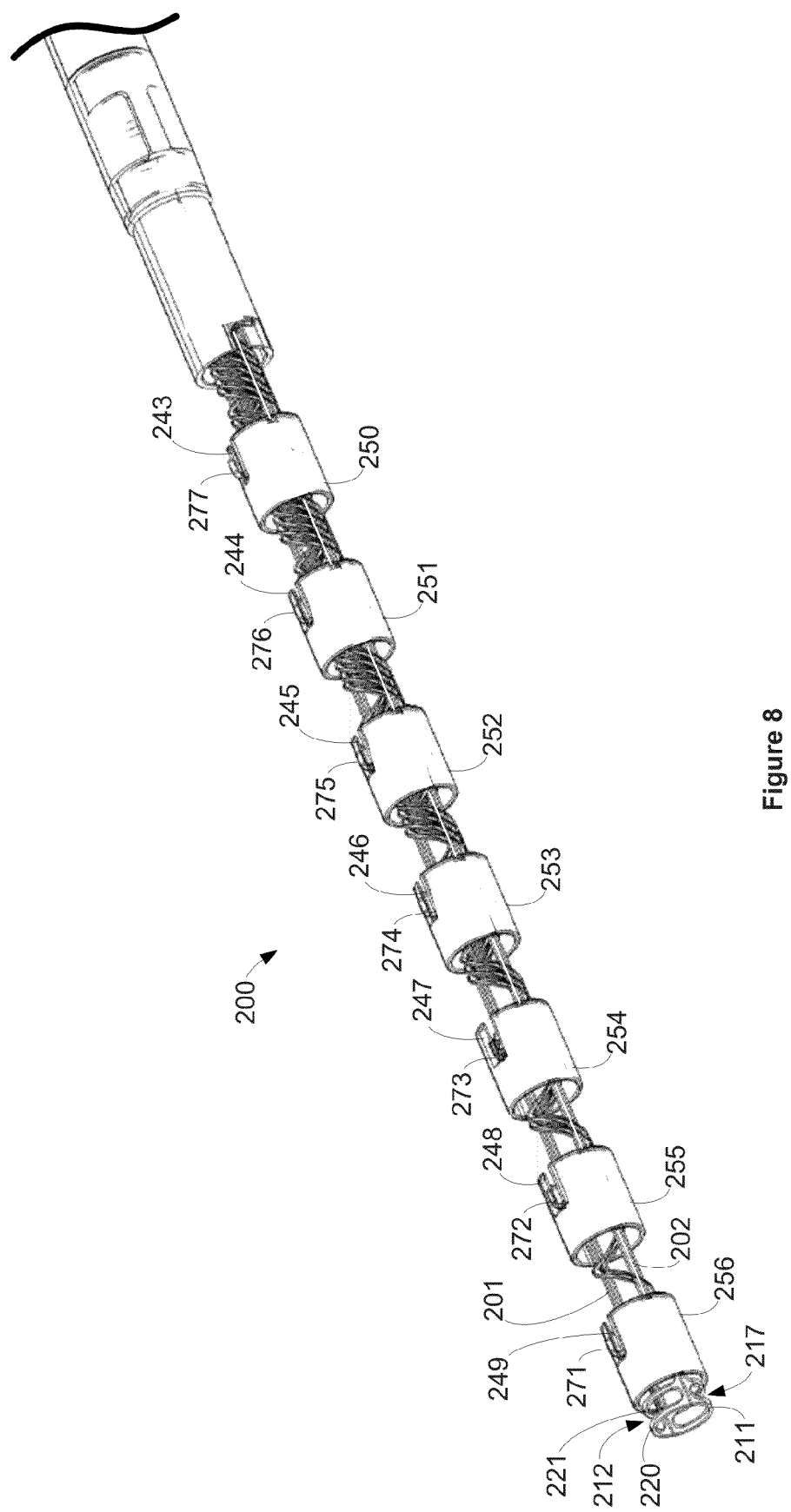
FIG. 8 illustrates a lead end subassembly fully loaded with electrical elements.

FIG. 8 shows that the support 200 has been fully loaded with electrical elements, in this case contact rings 250-256. Additionally, the proximal ends of conductors 271-276 have been placed in respective slots 244-249 of contact rings 251-256. The process for placing the contact rings 251-256 on the support 200, aligning the contact rings 251-256 with cross members 222-227, placing the proximal ends of the conductors 271-276 in slots 244-249, and welding the conductors 271-276 to the contact rings 251-256 can be done in the same manner as that of contact ring 250 or any other technique referenced herein.

Contact rings 250-256 are electrical elements. While contact rings 250-256 are shown as being loaded into the support 200 in FIG. 8, other electrical elements can additionally or alternatively be loaded onto the support 200. An electrical element, as used herein, refers to an electrically conductive component exposed on a lead and configured to deliver and/or receive electrical energy. Electrical elements can be any type of electrode, including rings and segmented electrodes.

As shown in FIG. 8, all of the contact rings 250-256 are on the support 200 and are further between at least some windows, cross members, and other grip features of the support 200. For example, window 212, defined by cross members 220 and 221 and longitudinal members 201 and 202, is proximal along the support 200 with respect to all of the contact rings 250-256. Moreover, window 209, defined by cross members 219 and 229 and longitudinal members 201 and 202, is distal along the support 200 with respect to all of the contact rings 250-256 (window 209 and cross members 219 and 229 are obscured in FIG. 8 by the zero contact 213 and polymer fill but are shown in FIG. 2). Corresponding windows are also located on the underside of the support 200 (e.g., window 217) and are respectively distal and proximal of the contact rings 250-256. As will be explained further herein, windows, cross members, and other aspects of grip features proximal and distal of contact rings provide attachment points fir polymer fill that will later be injected to fix the positions of the contact rings 250-256 by proximally and distally sandwiching the contact rings between polymer fill. As such, electrical elements such as contact rings 250-256, can be mechanically fixed between grip features, such as distal and proximal windows 209 and 212, by polymer fill.

As shown in FIG. 8, alignment between contact rings 250-256 and cross members 222-228 (shown in FIG. 2) provides for an array of contact rings 250-256 along the support 200. Specifically, the array of contact rings 250-256 has consistent spacing between the contact rings 250-256 due to the alignment with the cross members 222-228 of the support 200. Also, FIG. 8 shows that the contact rings 250-256 are axially aligned with each other, the support 200, and the zero contact 213. In particular, contact rings 250-256 are axially aligned because each is placed over respective cross members of the support 200. Each set of top and bottom cross members, such as cross members 222 and 232 or cross members 225 and 235, define a circular support structure over which respective circular contact rings 250-256 can be placed. The circular support structures provide some support and axial alignment for the contact rings 250-256 as the inner circular surface of each contact ring is placed over a respective circular support structure. There is some clearance between the inner surfaces of the contact rings 250-256 and the outer surfaces of the cross members 222-228 and 232-238. Enough clearance is provided to allow the contact rings 250-256 to slide over the circular support structures of the cross members 222-228 and 232-238. In some cases this clearance also allows polymer fill to penetrate and fill the space between the inner surfaces of the contact rings 250-256 and the outer surfaces of the cross members 222-228 and 232-238, as will be later described. In various embodiments, the clearance between the inner surfaces of the contact rings 250-256 and the outer surfaces of the cross members 222-228 and 232-238 is small enough to keep the contact rings 250-256 substantially axially aligned with each other and the support 200 by some contact between these surfaces. Axially aligned contact rings 250-256 provide a consistent and smaller profile for plugging a proximal lead end into an opening of a header. Moreover, axially aligned contact rings 250-256 can provided for tighter tolerances with seals of the header to keep fluids out of the header and from further penetrating between contact rings within the header.

In various embodiments, contact rings 250-256 are rotatable around the support 200 while in some other embodiments grooves or other features in the contact rings 250-256 and/or support 200 prevent rotation. Rotation of the contact rings 250-256 can be useful where the conductors 270 are run through the support 200 and the helical configuration of the conductors 270 makes it unpredictable how the individual filars will line up with the slots 243-249 of the contact rings 250-256. As such, in some embodiments the contact rings 250-256 can be rotated while on the support 200 to align the slots 243-249 with the respective angular positions of the filars at the longitudinal positions along the support 200 that the filer will be respectively cut.

In various embodiments, medical adhesive is used to temporarily tack the contact rings 250-256 in alignment on the support 200. For example, a medical adhesive can be applied to the proximal and/or distal ends of the contact rings 250-256 that line up with the longitudinal members 201 and 202. The medical adhesive is not intended to provide permanent fixation between the contact rings 250-256 and the support 200, but can provide temporary fixation until injection molding can permanently connect the contact rings 250-256 and the support 200. Adhesive options include epoxies.

A core pin (not illustrated) can be placed within the lumen of the subassembly shown in FIG. 8. Specifically, a metal pin can be inserted through the support 200, within the helical arrangement of conductors 270 (shown in FIG. 5), through the zero contact 213, and through some or the full length of the lumen of the main body. This subassembly, with the core pin, can be placed within a cavity of an injection mold die (not illustrated). The cavity can define a negative of a cylindrical lead. In particular, the cavity can define a negative of the lead proximal end 102 of FIG. 1. The inner diameter of the cavity can be slightly larger than the outer diameter of the contact rings 250-256 and zero contact 213, sufficient to accommodate the contact rings 250-256 and the zero contact 213 within the cavity. The inner diameter of the cavity can still be small enough to prevent polymer fill from flashing over the contact rings 250-256 or zero contact 213. Small ledges within the injection mold die may hold the contact rings 250-256 in place during injection of the polymer fill.

When the die of the injection mold is closed, typically by two plates coming together, polymer fill (e.g., polymer resin heated to allow the polymer material to flow) can be injected to fill in the cavity. The polymer fill can fill the entire space of the cavity thereby surrounding many of the components of the subassembly. Once the injection of polymer fill is complete, the die can be cooled (the polymer material solidifying as it cools) and the subassembly can be removed from the injection molding die. Gates from injection molding can be cut from the subassembly.

Figure 9:
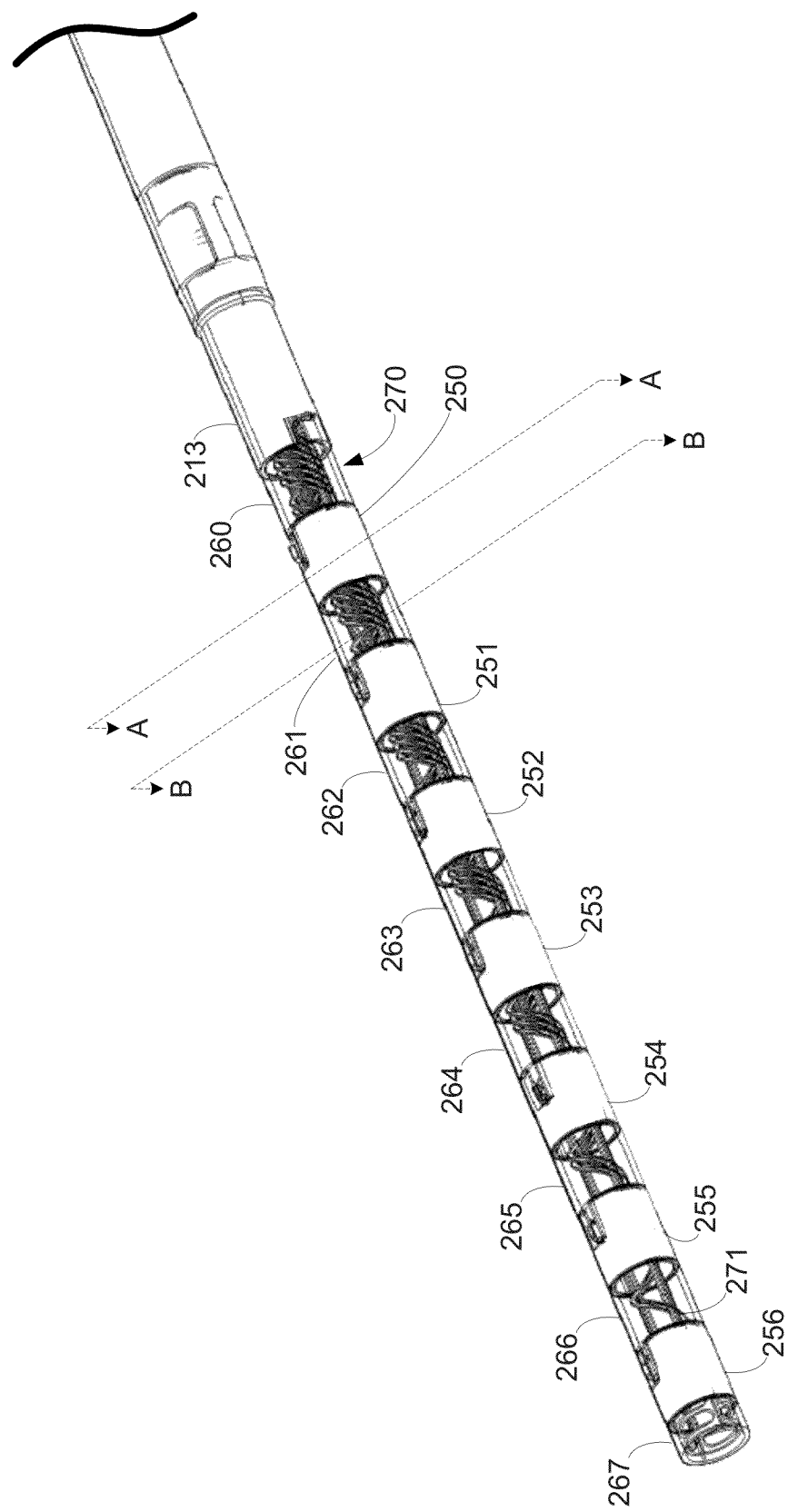
FIG. 9 illustrates a formed lead end.

FIG. 9 it illustrates a proximal end of a lead following injection molding as described above and after removal of the core pin. The interior space of the support 200 has been filled with now solid polymer fill, although a lumen remains because of the core pin. The conductors, such as conductor 271, have been encapsulated by the polymer fill. Also, the spaces between the contact rings 250-256 have been filled in with polymer fill. As a result, polymer sections 260-267 have been formed from the inner surface of the die cavity, forming a cylindrical shape that spans over the contact rings 250-256. The outer diameter of each of the polymer sections 260-267 is substantially the same as the outer diameter of the contact rings 250-256. As such, each of the contact rings 250-256 is in direct contact with polymer sections 260-267 proximally and distally. The contact rings 250-256 being surrounded proximally and distally by the polymer sections 260-267 fixes the contact rings 250-256, including fixing the axial alignment and spacing between the contact rings 250-256. The polymer fill has also penetrated the windows of the support 200, such as windows 207, 208, and 212, thereby allowing the polymer fill to mechanically connect to the support 200. The polymer fill acts as a web of material that is mechanically attached to the components of the lead end by surrounding some or all of the component surfaces. For example, the polymer fill spans underneath each of the contact rings 250-256 to bridge between each of the polymer sections 260-267. In various embodiments, the polymer fill will be continuous from the proximal end of the support 200 to the distal end of the support 200, thereby fixing the components around the support 200 and making a robust lead end. The end of the lead may be left open, as shown in FIG. 9, to allow access to the lumen of the lead, or it may be closed off, such as during injection molding or with a plug.

The support 200 adds stiffening strength to the lead end and the polymer fill mechanically binds the components of the lead end while also insulating various components. The section of a lead containing support 200, such as the lead proximal end 102 of FIG. 1, can be stiffer than the main body of the lead because of the presence of the support 200. In this way, the support 200 can add stiffness to a section of a lead where it is needed while leaving the remainder of a lead, such as a main body, flexible for conforming to an implant path in the body and moving with the body. The section of the lead containing the support 200 can still flex but will be stiffer then the sections of the lead that do not have a support 200. The use of metal to form the support 200 allows the support 200 to bend to some degree without yielding and to spring back to maintain a straight configuration. The ability of a proximal end of the lead to bend and spring back may be useful in inserting the proximal end into a header, in case an initial misalignment causes the proximal end to bend while the physician pushes the proximal end. It is noted that the support 200 will be substantially stiffer than conductors (e.g., cables, filars, coils, or other elongated conductive elements) within the lead. As such, in various embodiments, the stiffness of a lead end comes predominantly from the support 200 as compared to the stiffening contributions of other components of the lead end. It is noted that longitudinal members 201 and 202 that run the entire length of a support 200 can provide particular axial strength to improve the pushability of the lead end, such as when a physician is pushing a lead proximal end into a header.

The use of a metal support 200, onto which electrical elements such as contact rings 250-256 can be carried, opens up the interior space of the lead end to allow more volume of polymer fill during injection molding as compared to a lead end being built around a different material. Higher volume of polymer fill allows greater encapsulation of components within the lead end, such as conductors, which further strengthens the lead end and insulates electrical components. Moreover, higher volume of polymer fill allows for a harder pack of polymer material during injection molding, which makes for a denser, stronger, and stiffer lead end.

The polymer fill can be transparent. As shown in FIG. 9, conductors 270, such as conductor 271, can still be seen beneath the polymer fill within the polymer sections 260-267. It is also noted that the distal end of the zero contact 213 can likewise be seen under a coating of polymer fill from the first injection molding process. The polymer fill material may be, for example, opaque, colored, transparent, or non-transparent. The polymer fill may be polyether ether ketone (PEEK), polysulfone, urethane, and/or silicone, among other material types. In some cases epoxies or other adhesives or materials may be used in place of polymer fill to fill in the lead end.

Figure 10:
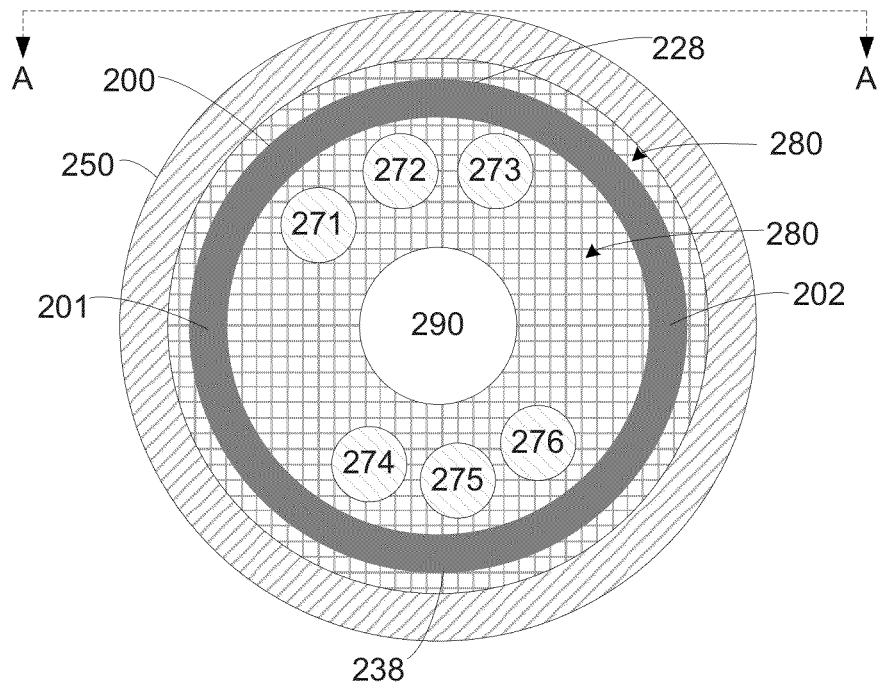
FIG. 10 illustrates a cross sectional view of a lead end.
Figure 11:
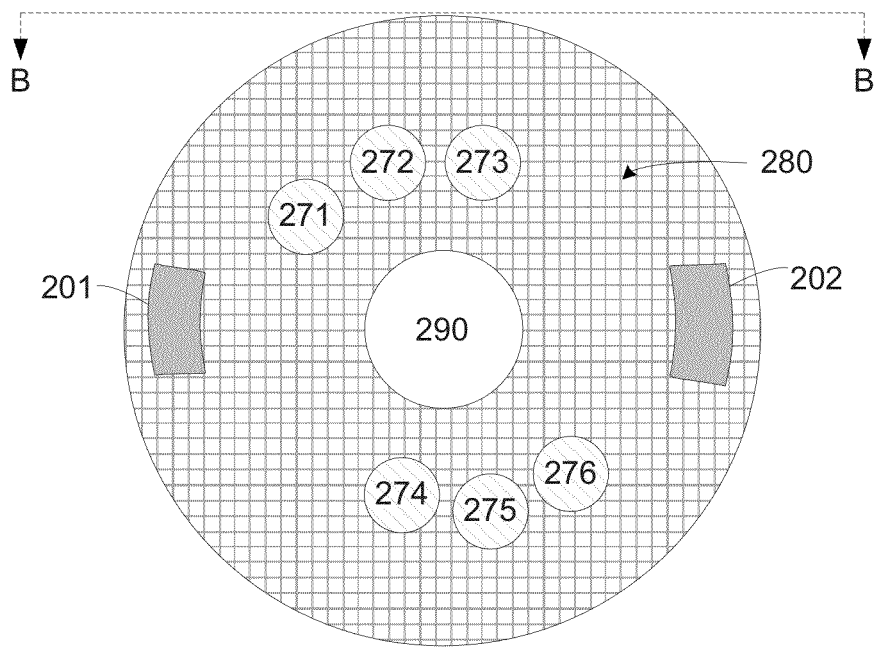
FIG. 11 illustrates a cross sectional view of a lead end.

FIGS. 10 and 11 illustrate AA and BB cross sections of FIG. 9, respectively. FIG. 10 shows the AA cross section slice that is taken through the contact ring 250 and support 200. Regarding the support 200, the AA cross section slice is taken through a section of the support 200 with a support ring formed by the upper arc cross member 228, lower arc cross member 238, and longitudinal supports 201 and 202. As such, support 200 is seen as a ring in the cross section of FIG. 10. Conductors 271-276 are also shown in FIG. 10, which are arrayed around the lumen 290 in a helical pattern. The lumen 290 was formed by the polymer fill 280 forming a cylindrical cavity around the core pin during injection molding.

Polymer fill 280 is shown by vertical and horizontal hash marks. As shown in FIG. 10, the polymer fill 280 defines the inner surface of the lumen 290, surrounds each of the conductors 271-276, is within the interior space of the support 200, surrounds the support 200, and is between the outer surface of the support. 200 and the inner surface of the contact ring 250. In various embodiments, one or more of the conductors 271-276 is not fully encapsulated by the polymer fill 280 (e.g., one or more of the conductors 271-276 may be pressed against one another or pressed against the support 200 or contact ring 250). However, in some embodiments the conductors 271-276 and/or the support 200 are fully encapsulated by polymer fill 280 for at least some length of the lead. In various embodiments, a support 200 may be fully encapsulated by polymer fill 280 for its entire length.

FIG. 11 shows the BB cross section slice that is taken through the polymer section 261, and as such the outer surface of the lead end is defined by polymer fill 280. As shown in FIG. 11, the outer surface of the polymer fill 280 takes on a circular shape, which is the same shape as the injection mold cavity negative. Other shapes, such as ovals and non-rounded shapes (e.g., having one or more flat sections such as a paddle, square, or rectangle shape) are also contemplated. The BB cross section slice includes the support 200 but only the longitudinal members 201 and 202 of the support 200 (e.g., no cross members). Conductors 271-276 are also shown in FIG. 11, which are arrayed around the lumen 290 in a helical pattern and are surrounded by polymer fill 280.

Figure 12:
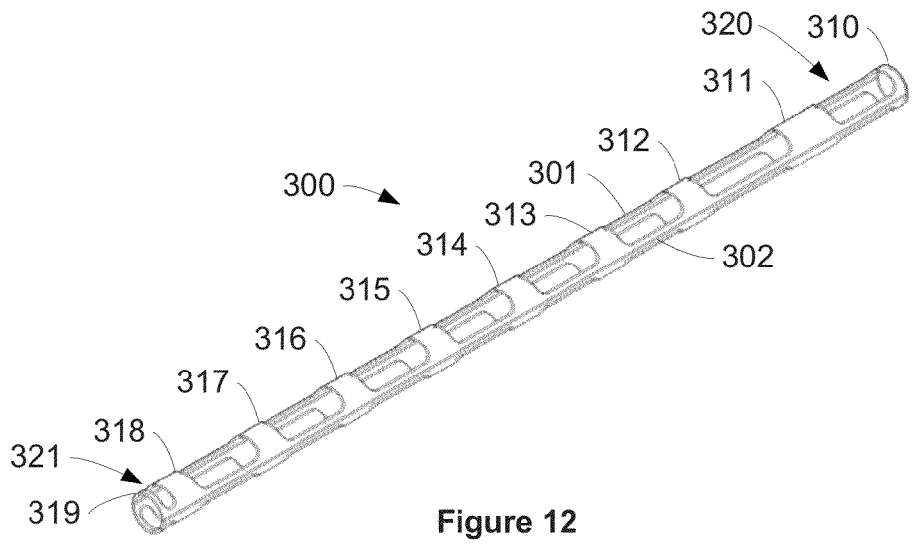
FIG. 12 illustrates an embodiment of a support.

FIG. 12 illustrates another embodiment of a support 300. The support 300 includes two longitudinal members 301 and 302 and a plurality or cross members, such as top cross members 310-319 and corresponding cross members on the underside of the support 300. Multiple windows are defined by the cross members and longitudinal members, such as window 320 defined by longitudinal members 301 and 302 and cross members 310 and 311. Window 321 is defined by longitudinal members 301 and 302 and cross members 318 and 319. Electrical elements (not shown) can be aligned with the cross members 310-319 as described herein. For example, ring electrodes or ring contacts can be slide over the support 300 and individually aligned with a respective cross member 310-319. In some cases, each electrical element will be between a distal window 320 and a proximal window 321, the windows providing grip elements for polymer fill material that prevents the electrical elements from movement along or off the support 300.

As elsewhere described herein, conductors can be moved through the interior space of the support 300, individually brought though respective windows, and welded to the electrical elements on the support 300. Additionally, an injection molding processes can be performed over the support 300 to mechanically connect a zero contact to the support 300 (e.g., as in FIG. 4) and to add polymer sections between electrical elements (e.g., as in FIG. 9). The support 300 of FIG. 12 has larger cross members 310-319 and longitudinal members 301 and 302 than those of support 200 of FIG. 2. Thicker members can result in a stiffer lead end. Larger members can also provide more surface area to support electrical elements placed on the support 300 before injection molding.

Figure 13:
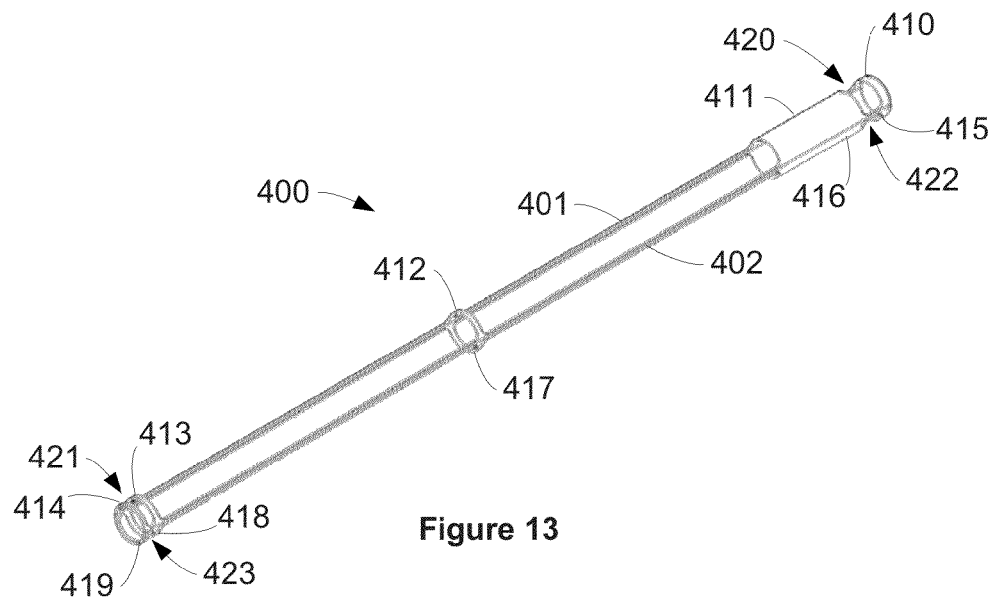
FIG. 13 illustrates an embodiment of a support.

FIG. 13 illustrates another embodiment of a support 400. The support 400 includes two longitudinal members 401 and 402 and a plurality or cross members, such as top cross members 410-414 and corresponding bottom cross members 415-419 on the underside of the support 400. Multiple windows are defined by the cross members and longitudinal members, such as window 420 defined by longitudinal members 401 and 402 and cross members 410 and 411. Window 421 is defined by longitudinal members 401 and 402 and cross members 413 and 414. Window 423, opposite window 421 on the underside of the support 400, is defined by longitudinal members 401 and 402 and cross members 418 and 419. Window 422, opposite window 420 on the underside of the support 400, is defined by longitudinal members 401 and 402 and cross members 415 and 416.

Support 400 provides few cross members for electrical element alignment, but in many implementations would be more flexible than supports 200 or 300 while still providing stiffening to a lead end. Support 400 also has fewer windows than supports 200 or 300, but more space for polymer fill. Support 400 provides windows 420-423 at distal and proximal ends of the support 400 to provide grip features for polymer fill distal and proximal to electrical elements arrayed along the support 400.

Figure 14:
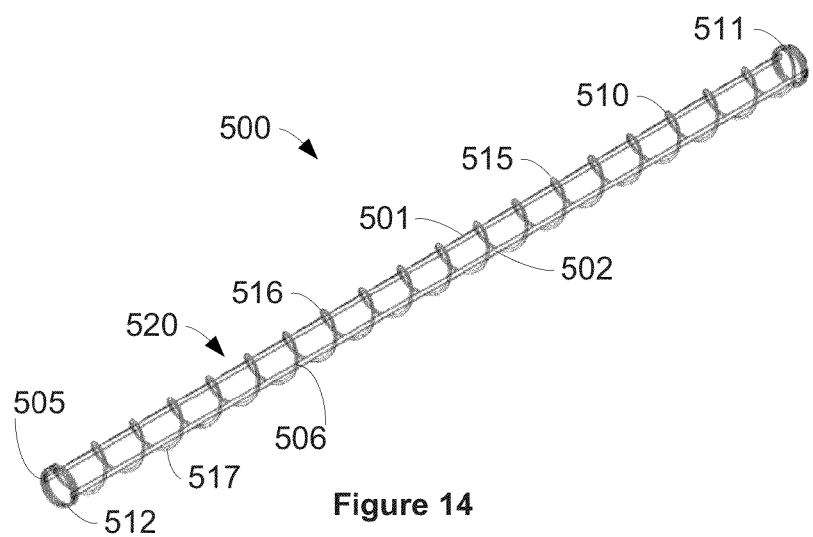
FIG. 14 illustrates an embodiment of a support.

FIG. 14 illustrates a support 500 composed of a spring 510 and two longitudinal members 501 and 502. The spring 510 can be made using any conventional technique for forming a spring. The longitudinal members 501 and 502 can be metal rods. The spring 510 can be welded to the longitudinal members 501 and 502 at various junction points. For example, the proximal end 512 of the spring 510 has a junction 505 with longitudinal member 501. A weld joint can be made at that junction 505. In this way, four welds can be made between junctions of the proximal end 512 and the distal end 511 of the spring 510. In some embodiments, only these welds will be made to form support 500. However, in some other embodiments, more or other junctions will be welded along the support 500, such as junction 506. In some embodiments, a weld will be made at each junction of contact between the spring 510 and either of the longitudinal members 501 and 502. Support 500 includes cross members, such as cross members 515-517. The cross members are not perpendicular to the longitudinal members 501 and 502 except on the distal end 511 and the proximal end 512. Each of the cross members can be a part of the spring spanning laterally from one side of the support 500 to the other side of the support 500. In some embodiments, each of the cross members can be a part of the spring spanning between one longitudinal member (e.g., 501 or 502) to the other longitudinal member (e.g., 501 or 502).

The supports 300, 400, and 500 can be used in the same manner as support 200 or in any way described herein. For example, any of supports 300, 400, and 500 can be overlapped by a zero contact and mechanically attached to the zero contact as in FIGS. 3-4. Any of supports 300, 400, and 500 can have conductors run through the interior space of the support 300, 400, or 500 as in FIG. 5. Any of supports 300, 400, and 500 can be loaded with electrical elements (e.g., contact rings) and have the conductors electrically and mechanically connected to the electrical elements (e.g., by welding) as in FIGS. 6-8. Any of these subassemblies can be injection molded to add polymer sections between electrical elements and fill any interior spaces with polymer fill as in FIGS. 9-11.

Figure 15:
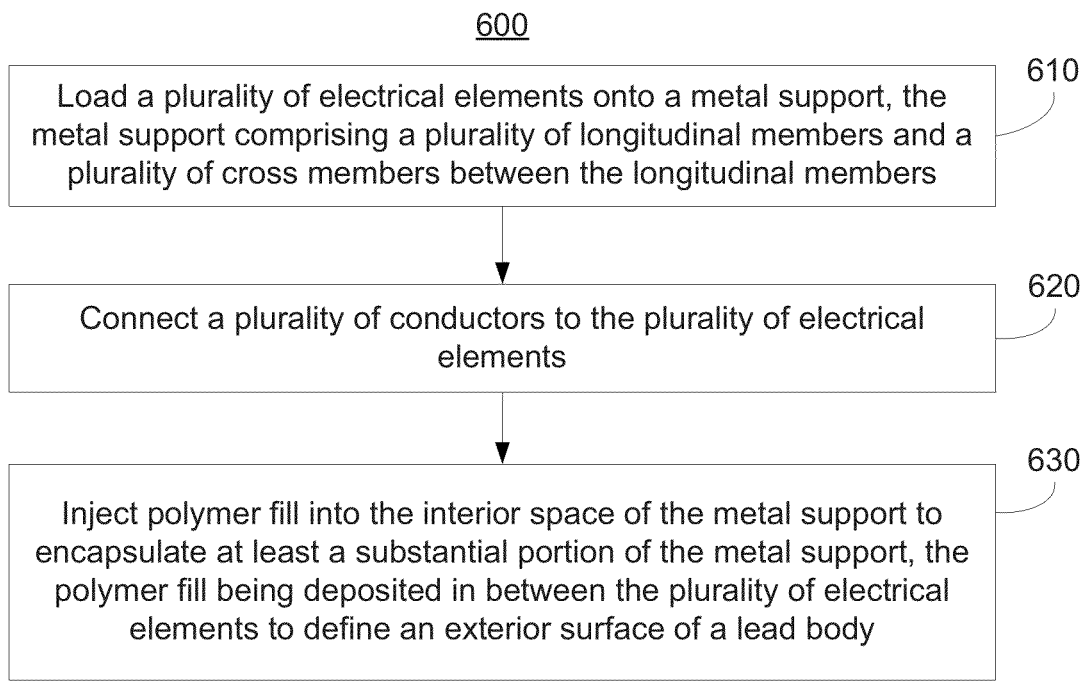
FIG. 15 illustrates a flow chart of a method of making a lead end.

FIG. 15 illustrates a flow chart of a method 600 for making a lead end. The method 600 can correspond to the steps described and illustrated in connection with FIGS. 2-11, for example. The method 600 includes loading 610 a plurality of electrical elements onto a metal support, the metal support comprising a plurality of longitudinal members and a plurality of cross members between the longitudinal members. As discussed herein, the metal support can have an interior space and can be electrically insulated by a coating. FIGS. 6-8 illustrate the loading 610 of electrical elements (contact rings 250-256 in this case) on a metal support (support 200).

The electrical elements loaded 610 onto the support can be any type of electrode and/or contact, such as a contact ring, electrode ring, or a segmented electrode, for example. A segmented electrode refers to an electrode that only spans around a limited portion of the circumference of a lead, and in some cases multiple segmented electrodes (e.g., three) are arrayed around the same circumference of a section of a lead. The electrical elements can be temporarily secured to the metal support by application of a fast curing medical adhesive between the metal support and each electrical element. The electrical element and the metal support can be permanently fixed to one another by injection molding as discussed herein. Segmented electrodes may have features such as loops or hooks on their underside, where injected polymer fill can encapsulate the features to mechanically attach the segmented electrode to the metal support and the rest of the lead.

The method 600 further includes connecting 620 a plurality of conductors to the plurality of electrical elements. Connecting 620 conductors and electrical elements can include welding a conductor to a respective electrical element such that each electrical element is mechanically and electrically connected to a different conductor. Other techniques for electrically connecting conductors to electrical elements are also contemplated, such as a mechanical crimp around a conductor, pinching a conductor between parts of an electrical element, or other technique for making a mechanical and electrical connection between a conductor and an electrical element. The conductors can be Mars, cables, coils, or any other elongated conductive component for conducting electrical signals. The conductors can be run through a subassembly of a lead body and though the interior space of the metal support, as in FIG. 5.

It is noted that in some embodiments, the conductors are connected 620 to respective electrical elements before the electrical elements are loaded 610 on the metal support. In which case, a conductor can be welded or otherwise connected 620 to an electrical element and then the conductor can be routed through the metal support and the lead subassembly as the electrical element is loaded 610 onto the metal support.

The method 600 further includes injecting 630 polymer fill into the interior space of the metal support to encapsulate at least a substantial portion of the metal support. In various embodiments, the polymer fill is deposited in between the plurality of electrical elements to define an exterior surface of a lead body. For example, the polymer sections 260-267 of FIG. 9 is composed of polymer fill that was deposited between electrical elements (which in the case of FIG. 9 are contact rings 250-256).

Although various embodiments described herein concern the use of injection molding, various embodiments may additionally or alternatively use a reflow process. Polymer cuffs can be loaded onto a support. The polymer cuffs can correspond to the polymer sections 260-267 of FIG. 9. The polymer cuffs can be loaded onto the support alternating with electrical elements (e.g., contact rings) or could be slit and put on the support after all of the electrical elements have been loaded onto the support. A shrink tube can then be placed over the polymer cuffs and the shrink tube heated (e.g., by a heat element or blowing hot air over the shrink tube). The shrink tube can shrink in response to the heat, applying pressure to the polymer cuffs while also transferring heat to the polymer cuffs. The polymer material can then flow into the support, it is noted that this technique may be used without polymer cuffs following an injection molding process (e.g., to the embodiment of FIG. 9) to smooth any edges.

Although the use of a support in the construction of a lead proximal end is used in many of the examples herein, it is noted that the same or similar construction techniques can be used to build a lead distal end using a support. For example, the technique of using support 200 in FIGS. 2-11 to build a lead end can be used to build either a lead proximal and/or distal end. In the case of building a lead distal end, the zero contact 213 may be replaced by another ring electrode. It is also noted that the number of electrical elements illustrated in the various Figures is not intended to limit the number of electrodes on a lead. End constructed around a support. One, two, three, four, ten, or any other number of electrical elements can be placed on a lead end using the techniques discussed herein.

Although the examples presented herein generally describe a single lead to conduct electrical energy between an IMD and tissue, multiple leads may be used in accordance with the devices and methods of the present disclosure. In some cases, multiple leads are used in parallel, where the multiple leads respectively connect to one IMD. In some cases, multiple leads are connected serially, where at least one of the leads serves as a lead extension. It is noted that the devices and methods presented herein are applicable to lead extensions and other leads that bridge electrical connections. For example, the construction of a proximal end and/or a distal end of a lead extension could be done in accordance with the present disclosure e.g., having an inner support), where the proximal end plugs into an IMD and the distal end mechanically and electrically connects with another lead. The distal and/or proximal ends of the lead mechanically and electrically connected with the lead extension can additionally or alternatively be constructed in accordance with the present disclosure (e.g., having an inner support).

The various techniques, features, and components discussed herein in various embodiments are applicable to various other embodiments in different configurations and combinations, as the present disclosure makes use of examples to illustrate options which are not limited to the specific embodiments presented. The present disclosure is presented using examples to illustrate and describe various aspects of a lead end having a spine. Each example and set of examples are presented herein to exemplify various features and options. As such, each example embodiment should be understood to be selectively combinable and modifiable in view of the other embodiments presented herein. The specific examples and options are therefore described in a broadening sense and not in a limiting sense.

We claim:

1. A lead, the lead comprising:
    a first end, a second end, and a main body connecting the first end and the second end, the first end having a first plurality of exposed electrical elements and the second end having a second plurality of exposed electrical elements, at least some of the exposed electrical elements on the first end respectively electrically connected to at least some of the exposed electrical elements of the second end by a plurality of electrical conductors in the main body;
    a metal support within the first end, the metal support comprising a plurality of longitudinal members generally parallel with the axis of first end of the lead and a plurality of cross members between the longitudinal members, wherein the metal support has an interior space, extends proximal and distal of the plurality of exposed electrical elements of the first end, and is electrically isolated from the exposed electrical elements of the first end; and
    polymer fill within the interior space of the metal support and encapsulating at least a substantial portion of the metal support, the polymer fill defining at least some of the exterior surface of the first end between the exposed electrical elements of the first end.

2. The lead of claim 1, wherein the metal support is a unitary body.

3. The lead of claim 1, wherein the cross members form a plurality of rings that are aligned axially with the axis of the first end of the lead.

4. The lead of claim 1, wherein the metal support comprises a plurality of grip features, each of the grip features comprising at least one of the cross members that is surrounded by the polymer fill to provide mechanical fixation between the polymer fill and the metal support.

5. The lead of claim 4, wherein at least one grip feature is located proximal along the lead with respect to the most proximal exposed electrical element of the first end and another grip feature is located distal along the lead with respect to the most distal exposed electrical element of the first end.

6. The lead of claim 1, wherein the metal support comprises a plurality of windows defined by the longitudinal members and the cross members.

7. The lead of claim 6, wherein the conductors run through the windows, the conductors bridging the electrical connections between the exposed electrical elements of the first and second ends.

8. The lead of claim 6, wherein each of the windows is filled in with the polymer fill.

9. The lead of claim 1, wherein each exposed electrical element of the first end comprises a contact ring that surrounds the metal support and defines at least some of the exterior surface of the first end.

10. The lead of claim 9, wherein each contact ring comprises a proximal end and a distal end, and the polymer fill directly contacts each of the proximal and distal ends of each contact ring to prevent the rings from moving proximally or distally along the lead.

11. The lead of claim 1, wherein the first end is configured to plug into an implantable medical device and the exposed electrical elements of the first end are arrayed to electrically connect with respective channels of the implantable medical device.

12. The lead of claim 1, wherein the lead further comprises a metal zero contact, the metal zero contact having a window and a flange, the metal zero contact at least partially overlapping with the support member, the metal zero contact being mechanically fixed to the metal support by the polymer fill filling the window of the metal zero contact.

13. The lead of claim 1, wherein the metal support provides a majority of the axial strength of the first end.

14. The lead of claim 1, further comprising a lumen within the first end and the main body, the lumen extending within the metal support and open on the first end of the lead.

15. The lead of claim 1, wherein the plurality of cross members comprise sections of a spring welded to the plurality of longitudinal members.

* * * * *